(12) United States Patent
Isokawa et al.

(10) Patent No.: US 9,478,021 B2
(45) Date of Patent: Oct. 25, 2016

(54) IMAGE DISPLAY DEVICE, IMAGE DISPLAY SYSTEM, AND IMAGE DISPLAY METHOD

(75) Inventors: Miho Isokawa, Tokyo (JP); Michio Oikawa, Tokyo (JP); Hiroki Taniguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 373 days.

(21) Appl. No.: 14/122,517

(22) PCT Filed: Apr. 5, 2012

(86) PCT No.: PCT/JP2012/059357
§ 371 (c)(1),
(2), (4) Date: Nov. 26, 2013

(87) PCT Pub. No.: WO2012/165044
PCT Pub. Date: Dec. 6, 2012

(65) Prior Publication Data
US 2014/0098092 A1    Apr. 10, 2014

(30) Foreign Application Priority Data

Jun. 1, 2011 (JP) ................................ 2011-123169

(51) Int. Cl.
| | |
|---|---|
| *G06T 15/00* | (2011.01) |
| *G06T 7/00* | (2006.01) |
| *G06T 15/08* | (2011.01) |
| *G06T 15/50* | (2011.01) |
| *A61B 5/00* | (2006.01) |

(Continued)

(52) U.S. Cl.
CPC ............. *G06T 7/0012* (2013.01); *A61B 5/742* (2013.01); *G06T 15/00* (2013.01); *G06T 15/08* (2013.01); *G06T 15/503* (2013.01); *A61B 5/055* (2013.01); *A61B 6/466* (2013.01)

(58) Field of Classification Search
None
See application file for complete search history.

(56) References Cited

U.S. PATENT DOCUMENTS

| | | | |
|---|---|---|---|
| 6,530,885 B1 * | 3/2003 | Entrekin | G01S 7/52053 128/916 |
| 2003/0210818 A1 * | 11/2003 | Abousleman | G06K 9/3233 382/199 |
| 2007/0098299 A1 | 5/2007 | Matsumoto | |

(Continued)

FOREIGN PATENT DOCUMENTS

| | | |
|---|---|---|
| JP | 07-146954 A | 6/1995 |
| JP | 2001-291090 A | 10/2001 |

(Continued)

*Primary Examiner* — Andrew G Yang
(74) *Attorney, Agent, or Firm* — Mattingly & Malur, PC

(57) ABSTRACT

An image display device comprises a first control part, a first storage, and a display part. The first storage holds rendering elements, each of which includes a combination of rendering target information and rendering setting information, and a priority order assigned to each rendering element. The rendering target information includes data identification information which designates three-dimensional data of a rendering target and mask information which designates a rendering target area. The rendering setting information includes information which designates a two-dimensional image rendering method and rendering parameter. The first control part determines, based on the rendering setting information and the mask information, whether executing priority processing is necessary. If it is determined that it is necessary to execute the priority processing, either the mask information or the rendering parameter is modified, and a two-dimensional image is rendered based on the rendering elements whereupon the priority processing is executed.

12 Claims, 12 Drawing Sheets

(51) Int. Cl.
*A61B 6/00* (2006.01)
*A61B 5/055* (2006.01)

(56) References Cited

U.S. PATENT DOCUMENTS

| | | | |
|---|---|---|---|
| 2008/0008371 A1* | 1/2008 | Woods | G06T 7/0012 |
| | | | 382/131 |
| 2008/0112602 A1 | 5/2008 | Azemoto et al. | |
| 2008/0150937 A1* | 6/2008 | Lundstrom | G06T 15/08 |
| | | | 345/419 |
| 2010/0201683 A1* | 8/2010 | Shirahata | G06F 19/321 |
| | | | 345/420 |
| 2011/0115785 A1* | 5/2011 | Miyamoto | A61B 6/466 |
| | | | 345/419 |
| 2011/0150178 A1* | 6/2011 | Bernard | G06T 11/008 |
| | | | 378/22 |
| 2012/0219198 A1* | 8/2012 | Mohr | G06T 7/0081 |
| | | | 382/131 |

FOREIGN PATENT DOCUMENTS

| | | |
|---|---|---|
| JP | 2001-291091 A | 10/2001 |
| JP | 2004-215846 A | 8/2004 |
| JP | 2007-014706 A | 1/2007 |
| JP | 2007-135843 A | 6/2007 |
| JP | 2008-119252 A | 5/2008 |

* cited by examiner

IMAGE DISPLAY DEVICE, IMAGE DISPLAY SYSTEM, AND IMAGE DISPLAY METHOD

CLAIM OF PRIORITY

The present application claims priority from Japanese patent application JP2011-123169 filed on Jun. 1, 2011, the content of which is hereby incorporated by reference into this application.

BACKGROUND OF THE INVENTION

This invention relates to rendering a medical image, and more particularly, to a setting, saving, and reusing technology for rendering a medical image with the use of three-dimensional data collected by a medical imaging machine such as a magnetic resonance imaging (MRI) machine (nuclear magnetic resonance image diagnostic machine) or a computed tomography (CT) machine.

The sophistication in the function of medical imaging machines such as MRI machines and CT machines in recent years has made collecting sectional images in large quantity possible. Medical image display devices, too, have been sophisticated in function, which has brought about an increase in speed and precision in the generation of three-dimensional data from sectional images, the rendering of a medical image from the three-dimensional data, and image processing on the medical image.

When interpreting a medical image (namely, making a diagnosis based on a medical image), selecting an appropriate method of rendering a medical image and adjusting a rendering parameter properly are necessary in order to facilitate the identification of a focus site. Executing this processing efficiently requires formulating information about the method of rendering and the rendering parameter (hereinafter referred to as rendering settings) into a pattern, and saving and reusing the settings pattern. It is also requested to improve the ease of understanding of a medical image and the precision of medical image interpretation by combining a plurality of rendering settings patterns flexibly and thus rendering a compositive medical image.

With regard to reusing a rendering settings pattern, Japanese Patent Application Laid-open No. 2001-291090 proposes a three-dimensional image display device that facilitates the pattern formulation and reproduction of image processing for creating a three-dimensional image, image diagnosis based on the three-dimensional image, treatment planning, and the like.

As a method of rendering an image by combining a plurality of rendering settings patterns, Japanese Patent Application Laid-open No. 2008-119252 proposes a method in which a plurality of display characteristics curves independent of one another are set to a part of an image that is within an observation target area, and are reflected at once. Japanese Patent Application Laid-open No. 2007-135843 proposes a method of generating and displaying an image in an area of interest and in other areas for which different rendering methods are used.

SUMMARY OF THE INVENTION

Formulating typical rendering settings into a pattern and reusing the pattern is one way to efficiently render a medical image with the use of three-dimensional data. However, there is a demand for being able to use only a part of a rendering settings pattern to suit the purpose of medical image interpretation and the characteristics of the subject, instead of using the rendering settings pattern as it is, and to generate a compositive medical image by combining a plurality of pieces of three-dimensional data or a plurality of rendering settings patterns.

In addition, when a compositive medical image is rendered by combining a plurality of pieces of three-dimensional data or a plurality of rendering settings patterns, rendering all simultaneously is not always possible, depending on the method of rendering and the positional relation of rendering target areas, and executing some priority processing with respect to rendering target areas or rendering settings patterns is required.

The conventional technologies described above cannot meet all of these requests.

According to this invention, there is provided an image display device, comprising: a first control part; a first storage; and a display part, wherein the first storage holds a plurality of rendering elements each of which comprises a combination of rendering target information, which specifies a rendering target, and rendering settings information, which is referred to when the rendering target is rendered, and holds a place in priority order assigned to each of the plurality of rendering elements, wherein the rendering target information comprises data identification information for specifying three-dimensional arrangement of signal values which are rendering targets, and mask information for specifying a rendering target area out of the three-dimensional signal value arrangement, wherein the rendering settings information comprises information for specifying a method of rendering a two-dimensional image based on the three-dimensional signal value arrangement, and information for specifying a rendering parameter to be applied to the rendering method, wherein the first control part is configured to: determine, based on the rendering settings information and the mask information, whether or not priority processing in which one of the mask information or the rendering parameter is modified needs to be executed; modify, when it is determined that the priority processing needs to be executed, the one of the mask information or the rendering parameter; and render a two-dimensional image based on the plurality of rendering elements that comprise the modified one of the mask information or the rendering parameter, and wherein the display part displays the two-dimensional image rendered.

According to one embodiment of this invention, the medical image based on the three-dimensional data can be displayed efficiently.

DETAILED DESCRIPTION OF THE PREFERRED EMBODIMENT

A medical image display device and a medical information management server are described below with reference to the accompanying drawings as an embodiment of this invention.

Figure 1:
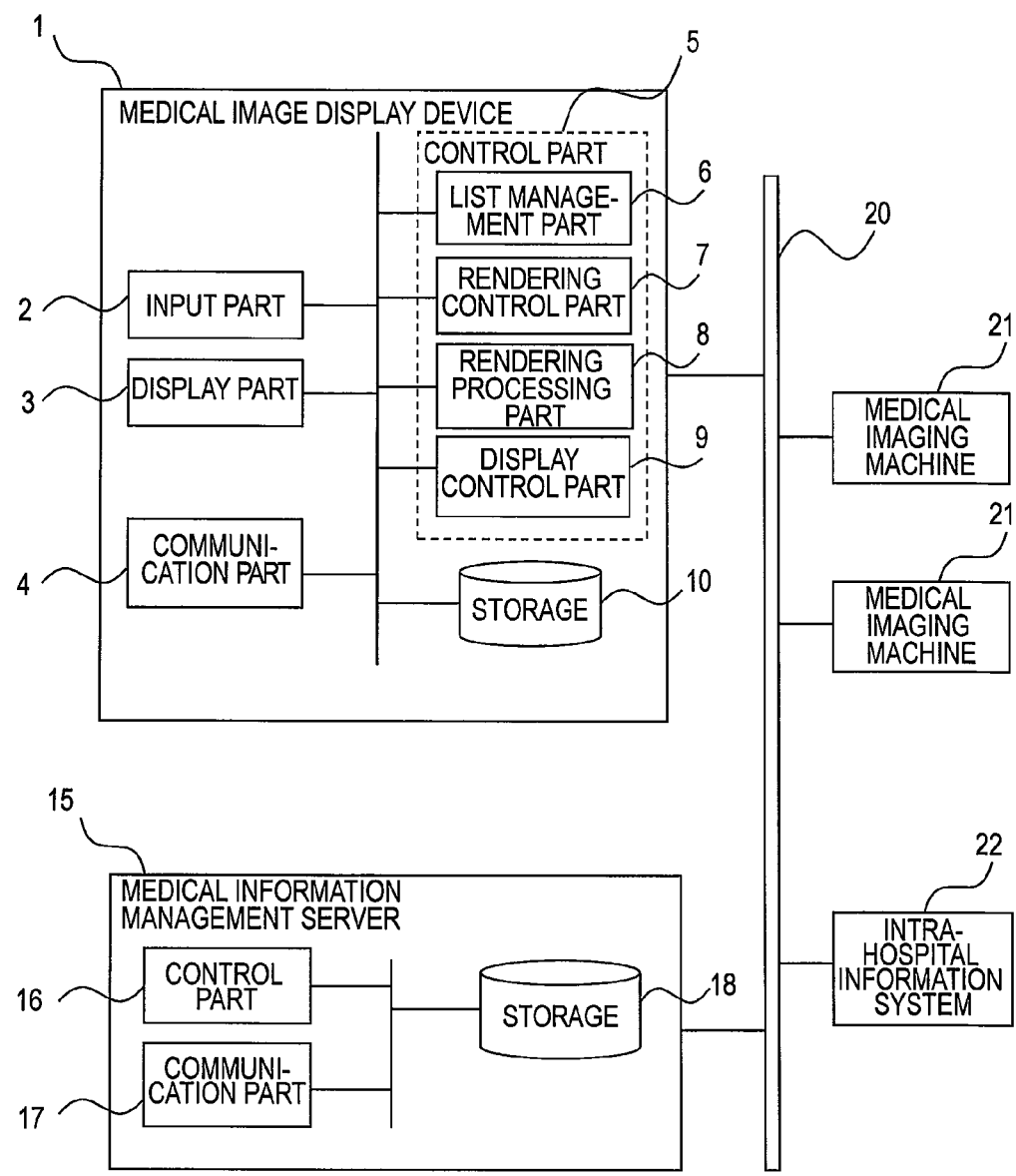
FIG. 1 is a block diagram illustrating an outline of the configurations of a medical image display device and medical information management server according to an embodiment of this invention.

The configurations of the medical image display device and medical information management server according to this embodiment are described first with reference to FIG. 1.

A medical imaging machine 21 such as an MRI machine or a CT machine collects sectional images (i.e., images made from signal values on cross sections) by image pickup, and transmits the images to a medical information management server 15 via a network 20. The network 20 may be, for example, an intranet of a hospital, a testing facility, or the like, or the Internet.

A medical image display device 1 is a computer device that is coupled to the medical information management server 15 to display an image such as a medical image generated by the medical imaging machine 21 by picking up a sectional image, or by rendering based on three-dimensional data that is constructed from a sectional image, so that a user can interpret the medical image or input diagnosis information. The medical image display device 1 includes, for example, a central processing unit (CPU), a memory, a read only memory (ROM), a hard disk drive (HDD), an input/output interface, a liquid crystal display (LCD), a keyboard, and a mouse.

The medical image display device 1 includes an input part 2, which processes an input from the user, a display part 3, which keeps a screen for displaying a medical image, a communication part 4, which transmits/receives information to/from the medical information management server 15 and an intra-hospital information system 22, a list management part 6, which manages a list of medical image interpretation orders, a medical information list, a user list, and the like, a rendering control part 7, which manages information related to rendering and executes priority processing, a rendering processing part 8, which executes processing of converting a sectional image and three-dimensional data, and renders, a display control part 9, which exerts display-related control such as managing the position of an element displayed on the screen, and a storage 10, which temporarily saves a medical image, rendering settings, diagnosis information, and the like. In the example of FIG. 1, the list management part 6, the rendering control part 7, the rendering processing part 8, and the display control part 9 are part of a control part 5. The control part 5 is implemented by, for example, by the CPU by executing a program that is stored in the memory. Therefore, processing executed by the control part 5 (i.e., the list management part 6, the rendering control part 7, the rendering processing part 8, or the display control part 9) in the following description is actually executed by the CPU following instructions of a program that is stored in the memory.

The medical image display device 1 may be a device whose main purpose is to enable one to view a medical image and diagnosis information, and does not include enabling one to interpret a medical image.

The medical information management server 15 is a Picture Archiving and Communication System (PACS: medical image diagnosis assisting system) server, and manages medical information such as a medical image, diagnosis information, and information about a patient. The medical information management server 15 includes a control part 16, a communication part 17, and a storage 18.

The control part 16 executes storing processing in which data received by the communication part 17 is stored in a database provided in the storage 18, retrieval processing in which data requested by a data request from the medical image display device 1 is obtained from a database provided in the storage 18, and the like. The control part 16 is implemented by, for example, a CPU and a memory.

The communication part 17 transmits/receives data to/from the medical image display device 1, the medical imaging machine 21, and the intra-hospital information system 22, which manages patient information, test information, accounting information, and other types of information.

The storage 18 is provided with a database for accumulating sectional images collected from the medical imaging machine 21, medical images generated by the medical image display device 1, rendering settings, diagnosis information, reports or similar types of information, information about patients obtained from the intra-hospital information system 22, and the like. The storage 18 is implemented by, for example, an HDD. The medical information management server 15 used may have the storage 18 that is provided with a database where all the pieces of information listed above are accumulated, or a plurality of medical information management servers 15 each having the storage 18 that is provided with a database where only particular information is accumulated may be used in cooperation with one another. Alternatively, the intra-hospital information system 22 that has an equivalent database may be used in cooperation with the medical information management server 15.

A configuration example of information about the rendering of a medical image is described next with reference to FIG. 2A to FIG. 3B.

Figure 2A:
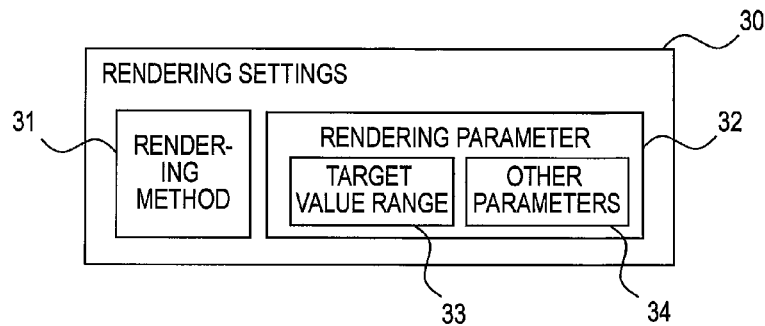
FIG. 2A is a diagram illustrating the data structure of rendering settings according to the embodiment of this invention.

Rendering settings 30 illustrated in FIG. 2A are information made up of a rendering method 31 and a rendering parameter 32.

The rendering method 31 is information for identifying the method of displaying a sectional image, or the method of performing projection processing on three-dimensional data. Concrete examples of how a sectional image is displayed include a method in which a sectional image obtained from the medical imaging machine 21 is displayed, and a method in which an arbitrary sectional image by Multi-Planar Reconstruction (MPR) is displayed. The projection processing of three-dimensional data is, to give a more detailed description, processing of projecting an image onto a two-dimensional screen based on the three-dimensional arrangement of signal values that are constructed from sectional images obtained by the medical imaging machine 21 (e.g., CT values). Examples of how this projection processing is executed include volume rendering (VR), surface rendering (SR), Maximum Intensity Projection (MIP), Minimum Intensity Projection (MinIP), and virtual endoscopy (VE). The following description of this embodiment deals with a rendering method in which the projection processing is performed on three-dimensional data. However, this invention is also applicable to a case where the rendering method used is a method in which a sectional image is displayed, and the rendering method 31 in that case contains information for identifying the method of displaying a sectional image.

The rendering parameter 32 is a parameter applied in order to display an image based on two-dimensional data that is generated by the rendering method described above. Specifically, the rendering parameter 32 includes a target value range 33, and other parameters 34 related to the rendering method 31.

The target value range 33 limits the range of signal values to which the other parameters 34 are applied with respect to the range of signal values measured by the medical imaging machine 21. For instance, the range of CT values (signal values measured by a CT machine) is about −2,000 to +4,000 in general and, in the case of setting the rendering parameter 32 for brains, a signal value range of about 60 to 90 is specified as the target value range 33. The other parameters 34 are not applied to signal values outside the specified range.

The other parameters 34 include, when the rendering method 31 is VR, for example, the window level, the window width, an opacity curve (namely, opacity allocation and color allocation to signal values), light source information, a view point in a three-dimensional space, and the like.

The rendering settings 30 are information that does not depend on a particular piece of three-dimensional data. Specifically, the rendering settings 30 that have been used to render an image from a piece of three-dimensional data can be reused to render a similar image from any other piece of three-dimensional data. The storage 18 or the like may store a plurality of rendering settings patterns 30 in the form of combinations of various rendering methods 31 and various rendering parameters 32.

Figure 2B:
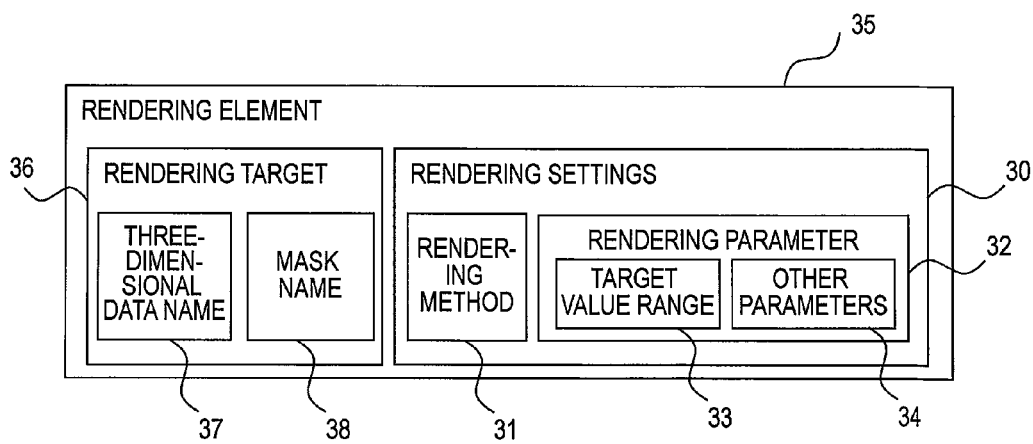
FIG. 2B is a diagram illustrating the data structure of a rendering element according to the embodiment of this invention.

A rendering element 35 illustrated in FIG. 2B is a combination of a rendering target 36 and the rendering settings 30. The rendering target 36 is information for specifying a target to which the rendering settings 30 are applied (namely, the target of the rendering based on the rendering settings 30), and includes a three-dimensional data name 37 and a mask name 38.

The three-dimensional data name 37 is information for identifying three-dimensional data (namely, the three-dimensional arrangement of signal values), and a piece of three-dimensional data to which the rendering settings 30 are applied is specified by this information.

A mask is information for specifying a rendering target area within a three-dimensional space to which three-dimensional data belongs, and contains, for each voxel (a coordinate grid point in a three-dimensional space) of the three dimensional data, binary data that indicates whether or not the voxel is a rendering target. The information volumes of three-dimensional data and a mask are large, which is why the rendering target 36 in this embodiment includes only names that are keys for calling three-dimensional data and a mask (i.e., a three-dimensional data name 37 and a mask name 38). However, the rendering target 36 may include three-dimensional data and mask data themselves.

The rendering element 35 is information about a particular piece of three-dimensional data, and is therefore used to reproduce rendering related to the particular piece of three-dimensional data, instead of being reused for another piece of three-dimensional data. The rendering element 35 may also be configured by allocating the rendering target 36 to the rendering settings 30.

The rendering settings 30 and the rendering element 35 are managed by the rendering control part 7, and the rendering processing part 8 executes rendering processing with the use of the rendering element 35. The rendering settings 30 and the rendering element 35 are saved by the rendering control part 7 in the storage 10 of the medical image display device 1, or the storage 18 of the medical information management server 15, to be called as the need arises and used as they are, or with a modification.

Figure 3A:
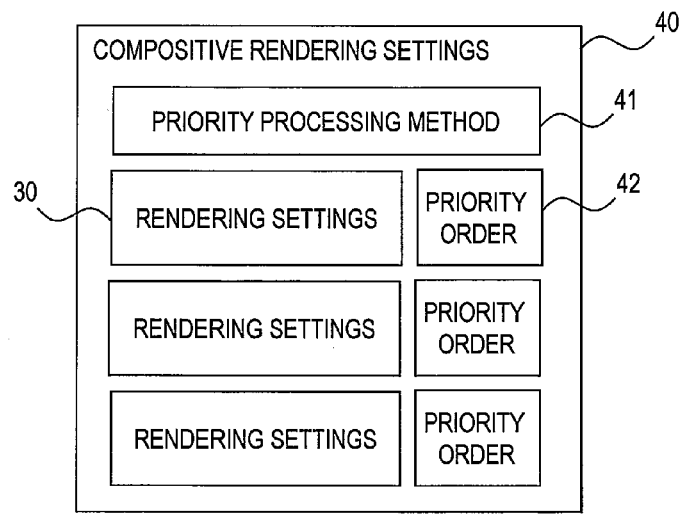
FIG. 3A is a diagram illustrating the data structure of compositive rendering settings according to the embodiment of this invention.
Figure 3B:
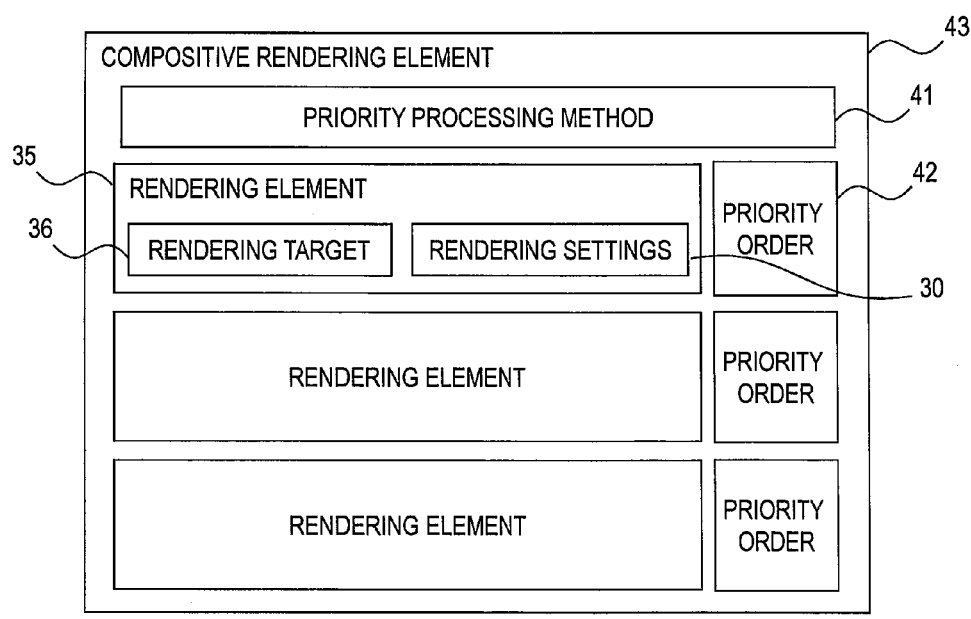
FIG. 3B is a diagram illustrating the data structure of a compositive rendering element according to the embodiment of this invention.

A compositive medical image can be generated from a set created by combining a plurality of rendering settings patterns 30, or a set created by combining a plurality of rendering elements 35. Compositive rendering settings 40 which are a set created by combining a plurality of rendering settings patterns 30 are illustrated in FIG. 3A. A compositive rendering element 43 which is a set created by combining a plurality of rendering elements 35 is illustrated in FIG. 3B. A compositive medical image is an image rendered in a state where a plurality of rendering settings patterns 30 or rendering targets 36 are present. For instance, using a different rendering settings pattern for each piece of three-dimensional data or for each specific area improves the ease of understanding and the precision of medical image interpretation.

The compositive rendering settings 40 are, similarly to the rendering settings 30, information that does not depend on a particular piece of data and can therefore be reused for an arbitrary piece of data. The compositive rendering element 43 can be, similarly to the rendering element 35, used to reproduce the rendering of an image. The compositive rendering element 43 may also be configured by setting the rendering target 36 to each rendering settings pattern 30 that is included in the compositive rendering settings 40.

Rendering processing is accomplished by creating a two-dimensional medical image from three-dimensional data through projection. For that reason, when mask areas that are specified by a plurality of rendering elements 35 included in the compositive rendering element 43 overlap on a projection ray and the rendering settings 30 in one mask area differ from the rendering settings 30 in another mask area, what calculation method is applied to signal values of voxels on the projection ray varies from one mask area to another. The resultant problem is that rendering cannot be executed unless the collision between calculation methods is dealt with.

The medical image display device 1 of this embodiment therefore performs some priority processing on each rendering element 35 before rendering. The priority processing here is processing of changing the compositive rendering element 43 based on priority in order to avoid the collision between calculation methods described above. To give a more detailed description, the priority processing is processing of changing mask areas or rendering parameters based on priority in order to avoid a collision between rendering methods or rendering parameters on a projection ray.

To execute this priority processing, a priority order 42 is attached to the rendering element 35 and information of a priority processing method 41 is attached to the compositive rendering element 43. The priority processing method 41 is information that defines a priority processing method to be applied, and may define priority processing individually for every combination of rendering elements, or may define, for each rendering element, priority processing for all rendering elements below the rendering element in question at once. The priority processing method 41 may specify one particular priority processing method, or may include all methods that can be selected as candidates so that a user can choose one of the candidates. In this embodiment, extended area excluding processing, area excluding processing, or rendering parameter integrating processing is defined as the priority processing method 41. Details of these priority processing methods 41 are described later.

The priority order 42 and the priority processing method 41 may be set not only to the compositive rendering element 43 but also to the compositive rendering settings 40. In the case where the compositive rendering element 43 is configured by allocating the rendering target 36 to the compositive rendering settings 40 to which the priority order 42 and the priority processing method 41 are attached, the priority order 42 and priority processing method 41 of the compositive rendering settings 40 may be used for the compositive rendering element 43 as they are, or may be modified before being used for the compositive rendering element 43.

In the case where a plurality of three-dimensional data names 37 included in the compositive rendering element 43 differ from one another, the priority processing described above is executed after positioning in the three-dimensional space. Possible cases where one three-dimensional data name 37 included differs from another are when the compositive rendering element 43 includes pieces of three-dimensional data generated from images of the same subject that have been taken at different times, when the compositive rendering element 43 includes pieces of three-dimensional data generated from images that have been taken by different medical imaging machines 21, and the like.

Not all items that constitute these rendering settings 30, the rendering element 35, the compositive rendering settings 40, and the compositive rendering element 43 need to be set. In the case where one of the items is not set, the item is treated as being in an initial state which is defined in advance, or as being not set yet. The rendering settings 30 may be treated as the compositive rendering settings 40 when only one rendering settings pattern 30 is included and the priority processing method 41 and the priority order 42 are not set. Similarly, the rendering element 35 may be treated as the compositive rendering element 43.

Figure 4:
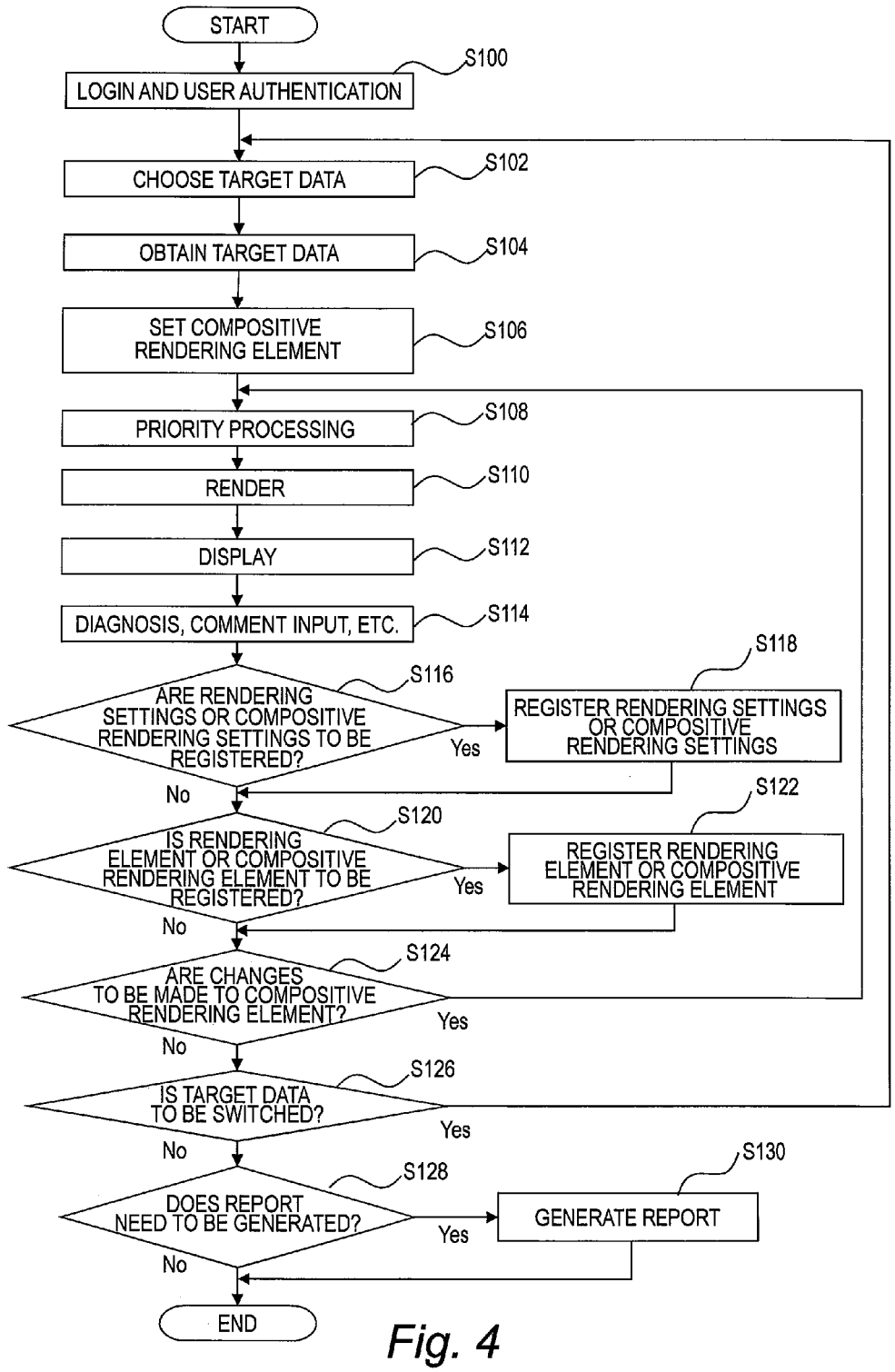
FIG. 4 is a flow chart illustrating processing for interpreting a medical image according to the embodiment of this invention.
Figure 5:
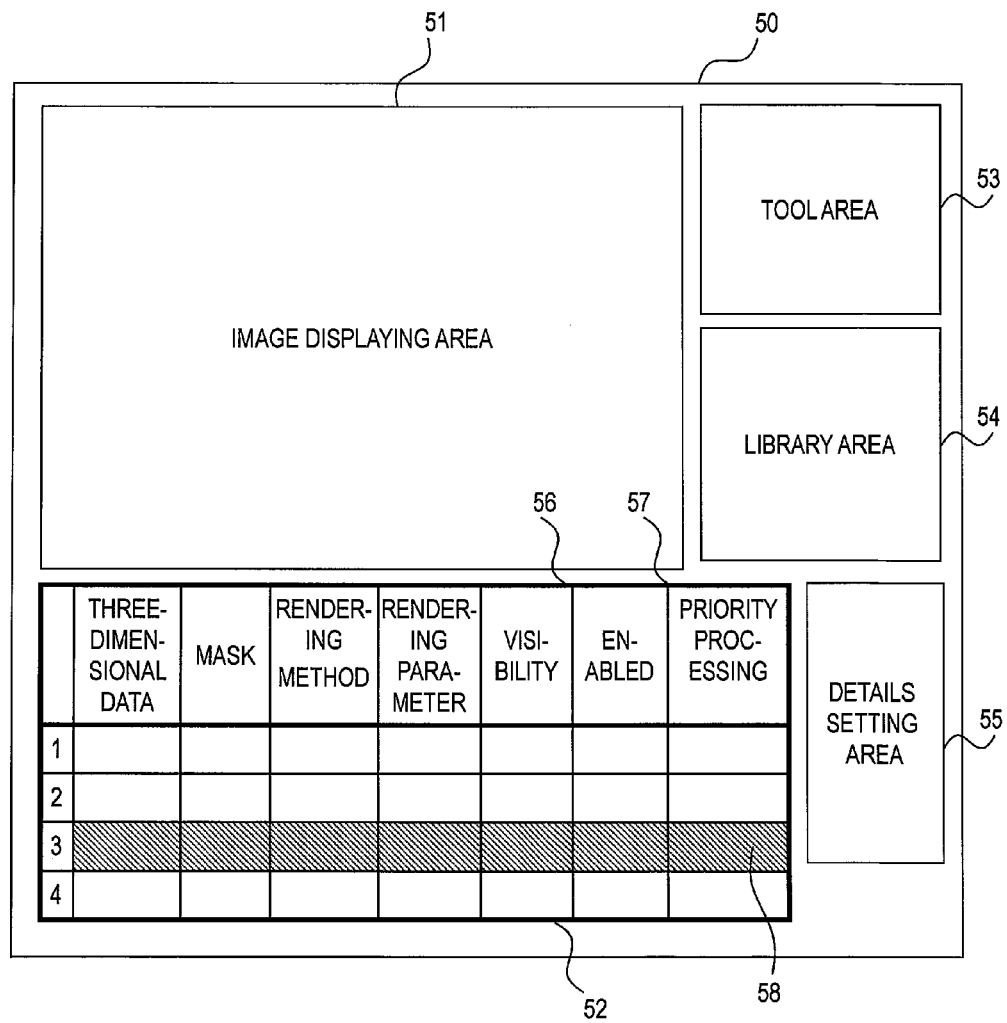
FIG. 5 is a diagram illustrating an example of a screen that is displayed by a display part according to the embodiment of this invention.

Described next with reference to FIG. 4 and FIG. 5 is an example of the flow of processing in which a user interprets a medical image with the use of the medical image display device 1 according to this embodiment. The description given here has in mind as the user a radiologist who has received a medical image interpretation order, or the like.

The input part 2 of the medical image display device 1 receives login processing from the user, and the list management part 6 then executes user authentication processing (S100). The list management part 6 generates a list of medical image interpretation orders and the user selects information of an interpretation target (S102). The description given here has in mind, as the interpretation target information, a set of sectional images collected by the medical imaging machine 21, three-dimensional data constructed in advance from the set of sectional images, a medical image rendered for three-dimensional data, the compositive rendering element 43 which includes three-dimensional data names, and the like. The interpretation target information may also be selected by the user by searching information that is accumulated in the medical information management server 15 with a patient name, a test name, an image set name, or the like as a key.

The communication part 4 transmits a data request that reflects the user's selection to the medical information management server 15. The medical information management server 15 searches the storage 18 for requested information (namely, the interpretation target information selected by the user), and transmits information that fits from the communication part 17 to the medical image display device 1. The communication part 4 of the medical image display device 1 receives the interpretation target information and, in the case where the information is a set of sectional images, the rendering processing part 8 constructs three-dimensional data from the set of sectional images, and accumulates the data in the storage 10 (S104).

The user next uses a compositive rendering element displaying area 52 and a details setting area 55 of a screen 50 (see FIG. 5), which is kept by the display part 26, to set the compositive rendering element 43 including at least one rendering element 35 that is a combination of the rendering method 31, the rendering parameter 32, the three-dimensional data name 37 of the interpretation target, and the mask name 38 (S106).

The display control part 9 displays in the compositive rendering element displaying area 52 a list of the rendering elements 35 that constitute the compositive rendering element 43 set (or to be set or to be changed) by the user. The rendering elements 35 are allocated rows of the list from the top downward in accordance with their respective places in priority order. Each row displays items that constitute the rendering element 35. When the user selects a row or an item with an input device such as a mouse, detailed information is displayed in a details setting area 55 so that modifications can be made. For an item that has not been set, a blank field or an indication that the item has not been set is displayed.

The compositive rendering element 43 may be set with the use of the compositive rendering settings 40 that are saved in advance in the storage 10 of the medical image display device 1 or the storage 18 of the medical information management server as settings patterns typical for different purposes of medical image interpretation. Alternatively, the compositive rendering element 43 may be set by using the compositive rendering settings 40 that have been selected as an initial value and modifying the initial value. A new compositive rendering element 43 may also be created. The compositive rendering element 43 that includes the three-dimensional data name 37 of the interpretation target may be called and used to set the compositive rendering element 43. The compositive rendering settings 40, the compositive rendering element 43, and other types of information saved in the storage 10 of the medical image display device 1 or the storage 18 of the medical information management server are generated by the list management part 6 and displayed in a library area 54 in response to the user's request.

The rendering processing part 8 generates a mask specified by the mask name 38 by an arbitrary method, and saves the mask in the storage 10. Examples of the arbitrary method include a method in which all voxels are set as a rendering target area, a method in which threshold processing is performed on the signal value of each voxel, a method in which the user manually selects an area with the use of a rendered medical image, a method in which an area growth method is used with a point specified by the user as the starting point, and a method in which a mask is called with the use of the mask name 38 of the rendering target 36 saved in the storage 10 of the medical image display device 1 or the storage 18 of the medical information management server.

In the case of performing threshold processing on the signal value of each voxel, a mask is generated so that an area of voxels whose signal values are larger (or smaller) than a given threshold out of all voxels is set as a rendering target area (namely, mask area). In the case where the user manually selects an area, a mask is generated so that the area selected by the user is set as a rendering target area.

After the user sets the compositive rendering element 43, the rendering control part 7 executes priority processing based on the compositive rendering element 43 (S108). The priority processing is described later (see FIG. 6). Next, the rendering processing part 8 renders an image (S110), and the generated medical image is displayed in an image displaying area 51 of the screen 50 (S112). The user consults the displayed medical image to make a diagnosis, and operates the medical image display device 1 by specifying a region of interest (ROI), entering a comment, or the like (S114).

When there is a possibility that the set compositive rendering settings 40, or the rendering settings 30 that constitute the set compositive rendering settings 40, might be reused for another piece of data, the user specifies the compositive rendering settings 40 or the rendering settings 30 to be reused in the compositive rendering element displaying area 52. The rendering control part 7 saves the specified compositive rendering settings 40 or rendering settings 30 in the storage 10 of the medical image display device 1 or the storage 18 of the medical information management server (S116 and S118). Similarly, when there is a possibility that the rendering result of this interpretation target might be reproduced later, the rendering control part 7 saves the compositive rendering element 43 or the rendering elements 35 (S120 and S122).

Items constituting the compositive rendering element 43 can be modified after the rendering processing as well. For instance, to make a plurality of types of diagnoses with the use of the same three-dimensional data, the rendering control part 7 can modify the specifics of the respective items of the compositive rendering element 43 to suit the respective purposes of the diagnoses. In the case where such modifications are made, the rendering processing is executed anew based on the modified compositive rendering element 43, and the displayed image is updated (S124).

In the case where the user wishes to interpret a medical image of another piece of data, S102 and the subsequent steps are executed anew, thereby switching the target data and rendering a new image (S 126).

In the case where a medical image interpretation report needs to be generated, the display control part 9 executes report generating processing with the use of the medical image rendered, an ROI or comment entered by the user, and the like (S128), registers the report in the storage 18 of the medical information management server 15 (S130), and then ends the medical image interpretation.

The priority processing (S 108) executed by the rendering control part 7 is described next in detail with reference to FIG. 6.

After the user sets the compositive rendering element 43 (S106), the rendering control part 7 checks the count of the rendering elements 35 that are included in the set compositive rendering element 43 (S200). When one rendering element 35 is included, only one mask area is set and there is no need to execute the priority processing. The rendering processing part 8 therefore renders an image (S110) without executing the priority processing. In the case where the compositive rendering element 43 includes two or more rendering elements 35, the rendering control part 7 executes the priority processing as needed (S202 to S216).

The rendering control part 7 first determines whether or not the compositive rendering element 43 includes the rendering element 35 for which the priority processing has not been performed (S202). Specifically, the rendering control part 7 determines, for each rendering element 35, whether or not priority processing between the rendering element 35 and the rendering elements 35 below the rendering element 35 in question has been executed. This determination is made based on the value of a priority processing flag, which is described later. When it is determined that priority processing between the rendering element 35 and its lower rendering elements 35 has not been executed with respect to at least one rendering element 35 (in other words, that the compositive rendering element 43 includes the rendering element 35 for which the priority processing has not been performed), the rendering control part 7 selects one of those rendering elements 35 that is highest in priority order (hereinafter referred to as rendering element A) (S204). In the following description, a rendering element that is assigned a higher place in priority order may also be simply referred to upper rendering element, and a rendering element that is assigned a lower place in priority order may also simply referred to as lower rendering element.

The rendering control part 7 next determines whether or not the compositive rendering element 43 includes the rendering element 35 that is below the rendering element A and that has not been processed by priority yielding processing (S206). Specifically, the rendering control part 7 determines, for each rendering element 35 below the rendering element A, whether or not priority processing between the rendering element 35 in question and the rendering element A (i.e., priority yielding processing) has been executed. This determination is made based on the value of a priority yielding processing flag, which is described later. When it is determined that the priority yielding processing has not been executed for at least one rendering element 35, the rendering control part 7 selects one of those rendering elements 35 that is highest in priority order (hereinafter referred to as rendering element B) (S208).

The rendering control part 7 next selects a priority processing method for the two selected rendering elements 35 (i.e., the rendering element A and the rendering element B) (S210). Specifically, in the case where one priority processing method is defined in advance by the priority processing method 41 of the compositive rendering element 43 for the two selected rendering elements 35, the rendering control part 7 refers to the defined method. In the case where a plurality of priority processing method candidates that can be selected are defined instead of one priority processing method, on the other hand, a message prompting the user to input is displayed. The user enters an instruction in which one of the priority processing method candidates is chosen to the input part 2.

The rendering control part 7 next executes the priority processing by a priority processing method that is selected for the rendering element B (S212), and sets "on" to the priority yielding processing flag of the rendering element B.

After selecting and executing the priority processing in a similar manner for every lower rendering element 35, the rendering control part 7 sets "on" to the priority processing flag of the rendering element A and sets "off" to the priority yielding processing flag of every rendering element 35 below the rendering element A (S216). When the priority processing flag of every rendering element 35 is "on", the rendering processing part 8 renders an image (S110).

The priority processing flag and the priority yielding processing flag (both are omitted from the drawings) are flags attached to each rendering element 35, and are managed internally by the rendering control part 7. The priority processing flag is a flag indicating whether or not priority processing between the rendering element 35 to which the flag in question is attached and every rendering element 35 below this rendering element 35 has been executed. A value "on" of the priority processing flag indicates that the priority processing has been executed. The priority yielding processing flag is a flag indicating whether or not priority processing between the rendering element 35 to which the flag in question is attached and a particular rendering element 35 above this rendering element 35 has been executed. A value "on" of the priority yielding processing flag indicates that the priority processing has been executed.

The selection of a priority processing method (S210) is described next with reference to FIG. 7, FIGS. 8A to 8C, and FIGS. 9A and 9B. The priority processing requires taking into consideration a situation in which mask areas overlap in the direction of a projection ray 60 with which an image is rendered. Situations in which a mask area 62 of the rendering element A high in priority order and a mask area 61 of the rendering element B low in priority order overlap each other are classified here into four patterns: one in which the two do not overlap and are not located on the same projection ray (in other words, no projection ray 60 passes through the two mask areas) (FIG. 8A); one in which the two do not overlap and are located on the same projection ray (in other words, at least part of the projection ray 60 passes through the two mask areas) (FIG. 8B); one in which there is an overlapping area 63 between the two (in other words, at least some of signal values belonging to one of the mask areas belong to the other mask area as well) (FIG. 8C); and one in which the two coincide with each other completely (in other words, the two mask areas overlap entirely) (not shown).

Figure 6:
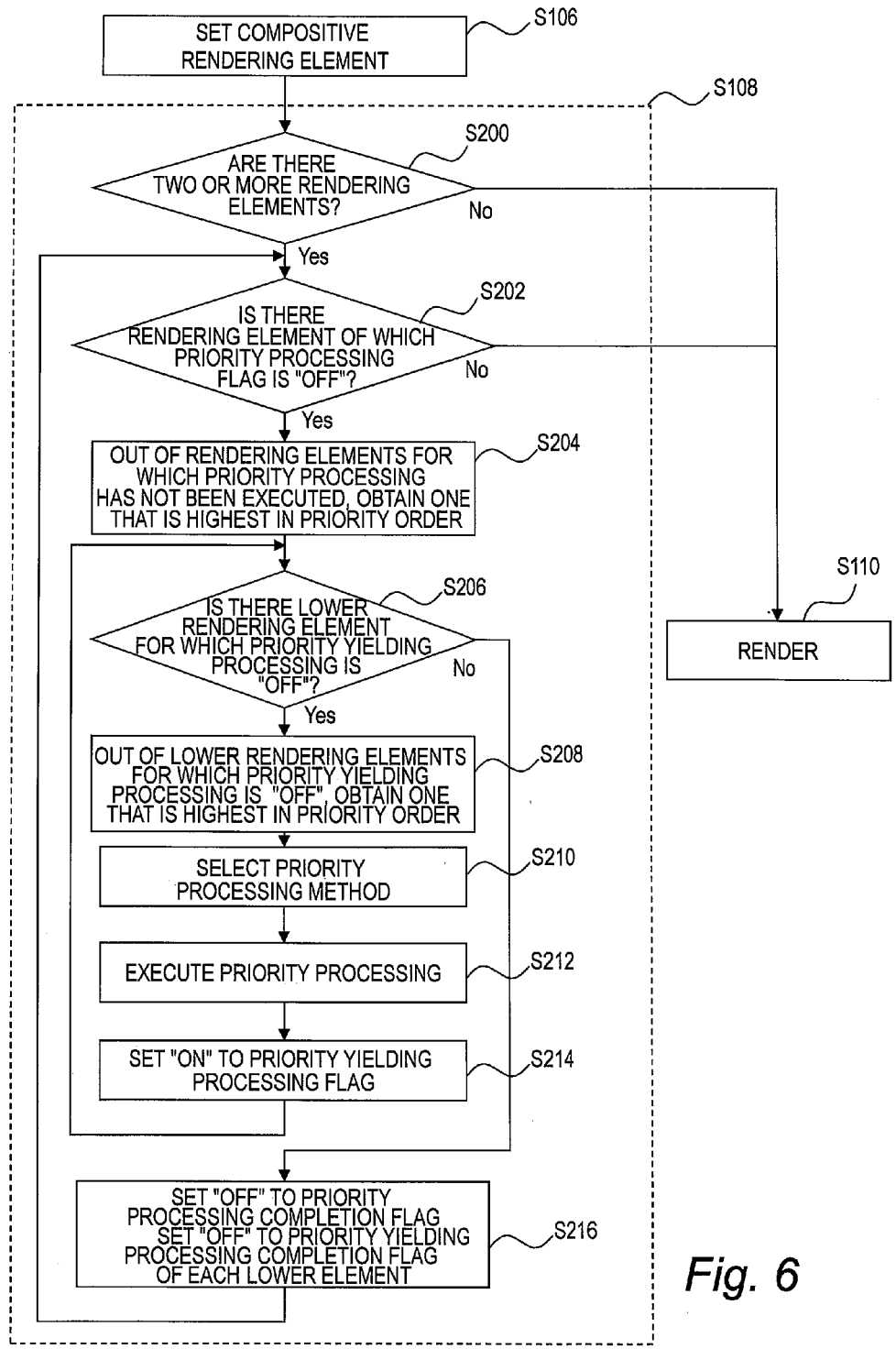
FIG. 6 is a flow chart illustrating steps of priority processing of a compositive rendering element according to the embodiment of this invention.
Figure 7:
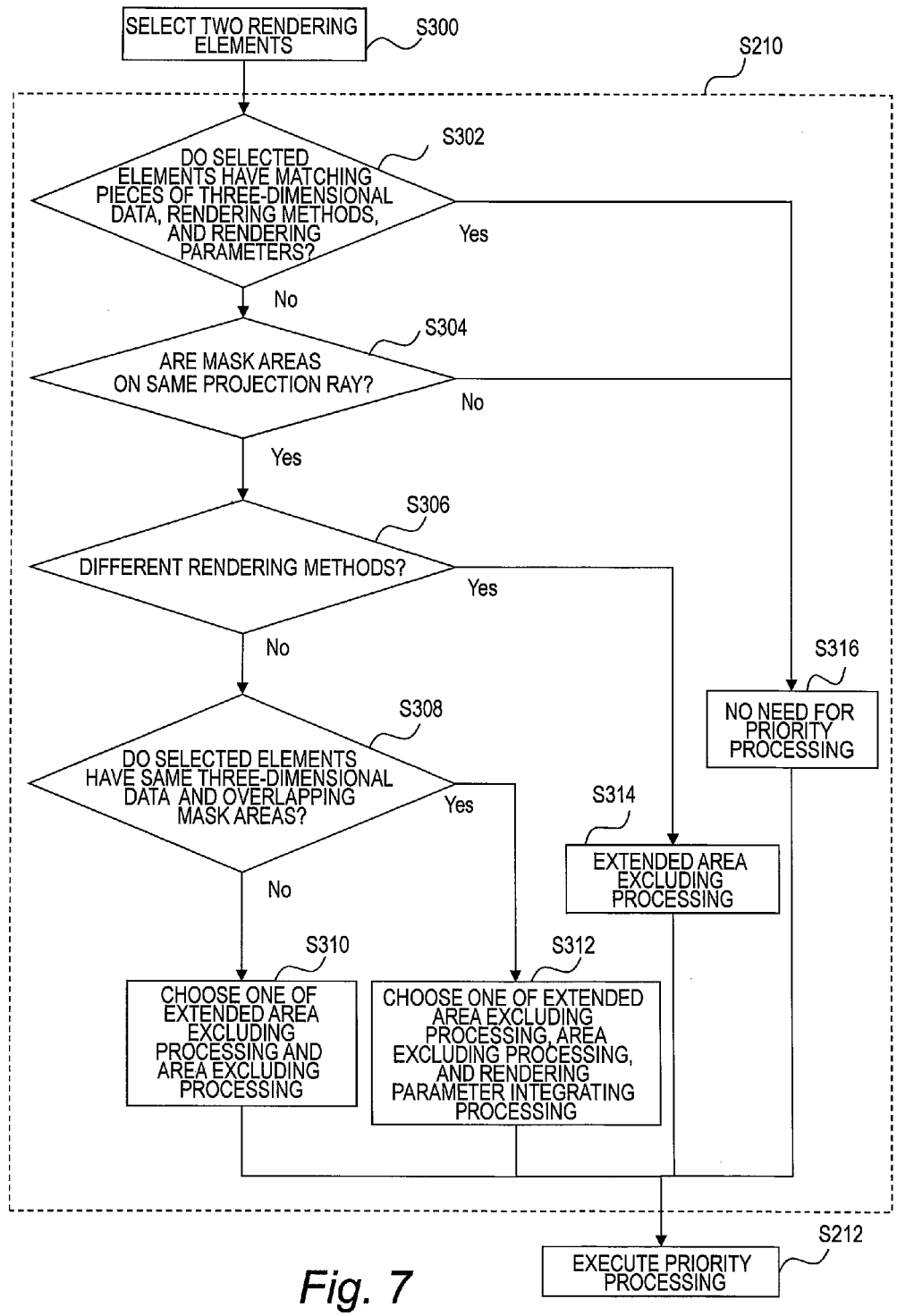
FIG. 7 is a flow chart illustrating a selection step of the priority processing according to the embodiment of this invention.
Figure 8A:
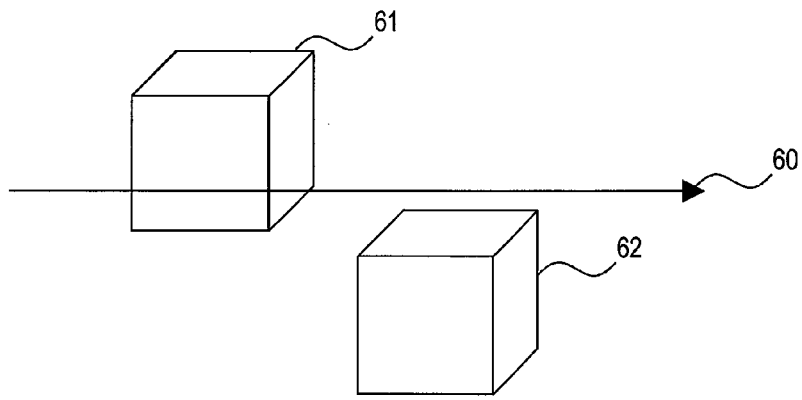
FIG. 8A is a diagram illustrating two mask areas according to the embodiment of this invention that are not on the same projection ray.
Figure 8B:
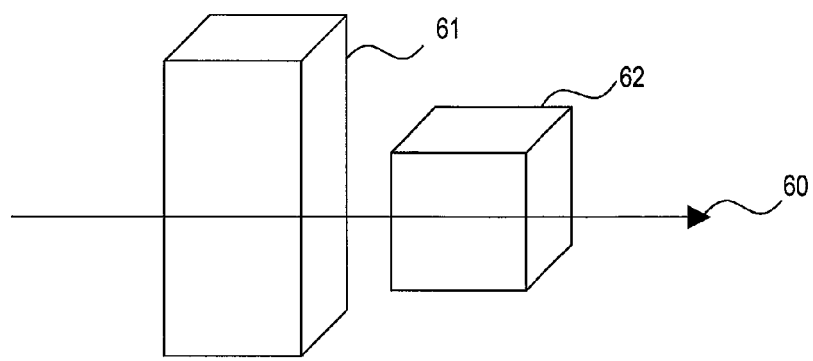
FIG. 8B is a diagram illustrating two mask areas according to the embodiment of this invention that are on the same ray.
Figure 8C:
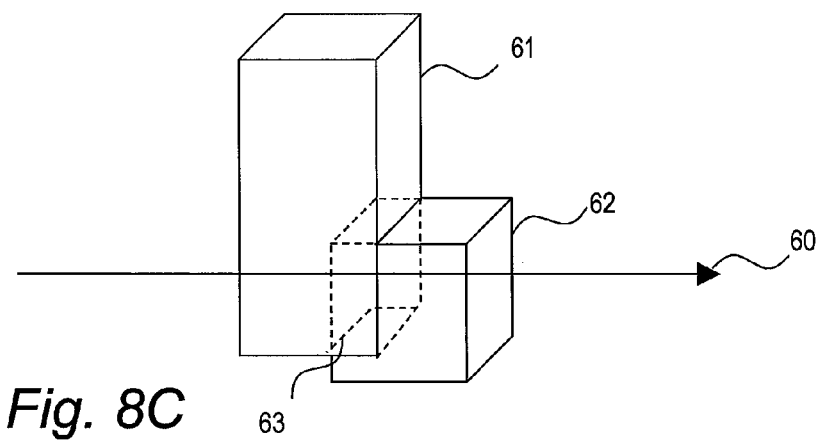
FIG. 8C is a diagram illustrating two mask areas according to the embodiment of this invention that overlap each other.
Figure 9A:
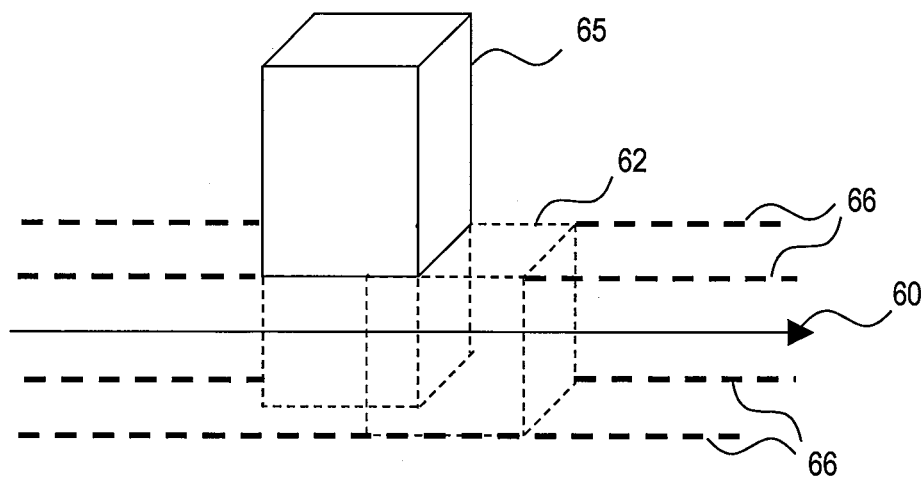
FIG. 9A is a diagram illustrating extended area excluding processing according to the embodiment of this invention.
Figure 9B:
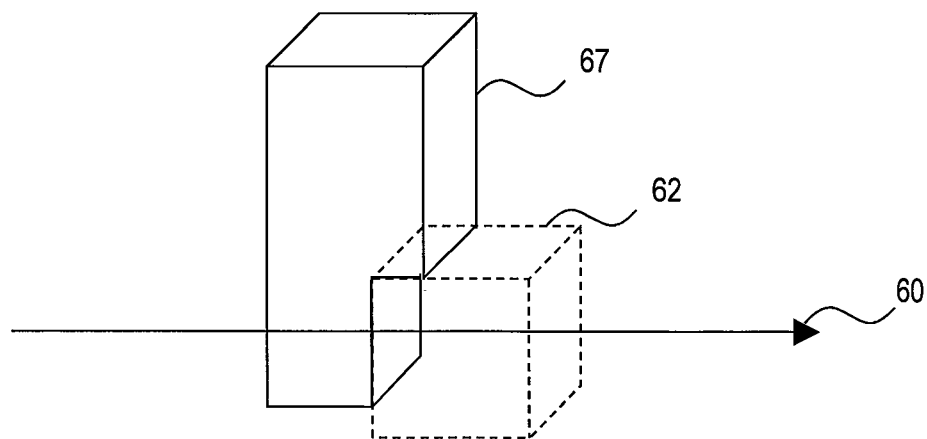
FIG. 9B is a diagram illustrating area excluding processing according to the embodiment of this invention.

The selection of two rendering elements in FIG. 7 (S300) corresponds to S202 to S208 of FIG. 6. In the case where pieces of three-dimensional data, rendering methods, and rendering parameters of the two rendering elements all match (S302), rendering processing can be executed without performing the priority processing whatever the mask area overlapping situation is. It is therefore determined that executing the priority processing is unnecessary (S316). The execution of the priority processing is determined as unnecessary also when the two mask areas do not overlap and are not located on the same projection ray (FIG. 8A, S304 of FIG. 7) and there is accordingly no fear that a plurality of rendering methods are applied on the same projection ray (in other words, no collision between a plurality of rendering methods or a plurality of rendering parameters) (S316).

In other cases than those described above, a collision occurs between a plurality of rendering methods or a plurality of rendering parameters, and needs to be avoided by executing the priority processing.

First, in the case where different rendering methods are applied (S306), the rendering control part 7 executes extended area excluding processing as the priority processing so that only one rendering method is applied on the same projection ray. The extended area excluding processing is processing that is executed when two mask areas specified by the two rendering elements 35 are at least partially on the same projection ray to remove a portion on the same projection ray from one of the two mask areas that is specified by the lower rendering element 35. More specifically, the extended area excluding processing is processing of removing an area that is an extension of the mask area 62 of the high-priority rendering element A in a direction parallel to the projection ray 60 (the area indicated by broken lines 66) from the mask area 61 of the low-priority rendering element B, and setting the resultant area as a mask area 65 on which the priority yielding processing of the rendering element B has been executed.

This mask area modification is executed by, for example, newly creating information for specifying the mask area 65 and changing the mask name 38 that is included in the rendering target 36 of the rendering element B from the name of the mask area 61 to the name of the mask area 65. The same applies to area excluding processing, which is described later.

In the case where the priority processing is necessary and the two mask areas use different rendering methods, the extended area excluding processing is selected automatically. A collision between rendering methods on a projection ray is thus solved.

In the case where the priority processing is necessary and the two mask areas use the same rendering method, the rendering control part 7 chooses one of the extended area excluding processing described above and area excluding processing that suits the purpose (S310). The area excluding processing is processing that is executed when two mask areas specified by the two rendering elements 35 overlap at least partially to remove the overlapping portion from one of the two mask areas that is specified by the lower rendering element 35. More specifically, the area excluding processing is processing of removing an area that overlaps with the mask area 62 of the high-priority rendering element A from the mask area 61 of the low-priority rendering element B, and setting the resultant area as a mask area 67 on which the priority yielding processing of the low-priority rendering element B has been executed. A collision between rendering parameters in an overlapping area is thus solved.

However, in the case where the priority processing is necessary, the two mask areas use the same rendering method, the two rendering elements have the same three-dimensional data, and the mask areas overlap at least partially (S308), a collision between rendering parameters in the overlapping area 63 may be solved by selecting processing of integrating the rendering parameters 32 for the overlapping area 63, instead of the extended area excluding processing and the area excluding processing (S312). The rendering parameter integrating processing is processing that is executed when two mask areas specified by the two rendering elements 35 overlap at least partially to create a new rendering parameter by integrating the two rendering parameters 32 that are associated with the mask areas, and to switch the rendering parameter of the overlapping area to the new rendering parameter. Details of the rendering parameter integrating processing are described later (see FIG. 10).

In the case where priority processing can be selected from a plurality of candidates, the user chooses one that suits the purpose of diagnosis by taking into account what medical image is being requested. A medical image rendered by executing the extended area excluding processing does not have an overlapping area to which different rendering methods and different rendering parameters are applied. The extended area excluding processing is therefore used when, for example, a particular area is displayed by VR rendering whereas other areas are displayed by MIP rendering.

The area excluding processing, on the other hand, is used when only a single rendering settings pattern 30 is applied to each mask area. In the case where mask areas of respective rendering elements do not overlap in a three-dimensional space but are on the same projection ray, an image is rendered by using both rendering settings during projection processing. The area excluding processing is used when, for example, a different opacity curve is set for each mask area and the entire image is rendered by VR.

The rendering parameter integrating processing is used when a plurality of rendering elements have the same rendering method and different rendering parameters, mask areas of the rendering elements coincide or at least partially overlap with one another, and rendering processing is executed by integrating the plurality of rendering parameters and applying the resultant rendering parameter to the overlapping area. The area excluding processing and the extended area excluding processing are not performed on the overlapping area in this case. Here, rendering parameters are integrated into one by removing a range of target values of the high-priority rendering element A from a range of target values of the low-priority rendering element B, and the resultant rendering parameter is applied to the overlapping area 63. The rendering parameter integrating processing is used when, for example, an image is rendered by VR by selecting from the storage 10 a plurality of rendering settings patterns that include opacity curves for displaying a particular site or organ, allocating the rendering settings patterns to the respective rendering elements, and rendering the whole image with an opacity curve that is obtained through the integration of the rendering settings patterns.

Figure 10:
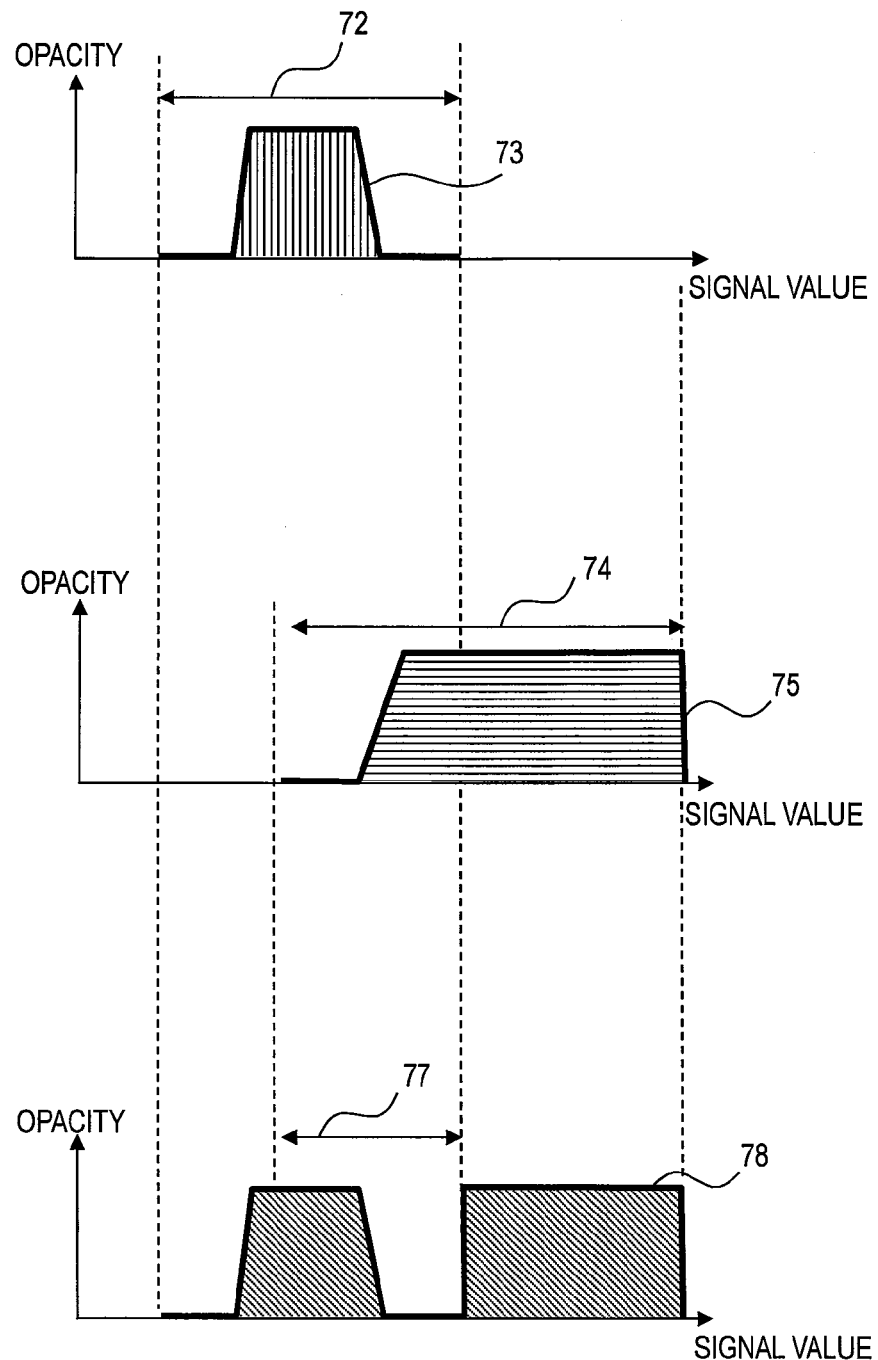
FIG. 10 is a diagram illustrating processing of integrating opacity curves according to the embodiment of this invention.

An example of using the rendering parameter integrating processing is described in detail with reference to FIG. 10. The example used here is the compositive rendering element 43 which includes a plurality of rendering elements 35 that have the same three-dimensional data and rendering method (specifically, RV) and different masks and rendering parameters (specifically, opacity curves 73 and 75) from one another. VR is a rendering method in which pixel values on a screen are calculated for signal values of three-dimensional data on a projection ray by taking into account the opacity, color, and light attenuation of signal values that are defined by an opacity curve in order from the forward.

Each rendering element 35 includes the specification of the range of rendering target signal values (namely, the target value range 33). The opacity curves 73 and 75 are modified so that, when mask areas of two rendering elements 35 overlap and the rendering target signal value ranges overlap in the overlapping area 63, the opacity curve 73 specified by the rendering element 35 that is high in priority order is applied in the overlapping signal value range, which is denoted by 77, whereas the opacity curve specified by one of the rendering elements 35 (namely, the opacity curve 73 or 75) is applied to the other as well in signal value ranges that do not overlap.

Specifically, on opacity curves that have signal value on the axis of abscissa, a value range 72 of the upper rendering element in priority order is removed from a value range 74 of the lower rendering element, to thereby eliminate the overlapping of value ranges, and an integrated opacity curve 78 is generated by integrating the opacity curves 73 and 75 in the respective value ranges. In the area where the masks overlap, calculation processing of VR is executed with the integrated opacity curve 78, instead of the opacity curve 73 or 75, and the opacity curves 73 and 75 set by the respective rendering elements are used in areas where the masks do not overlap to execute calculation processing of VR.

An opacity curve is set, for example, as follows. The user chooses a particular rendering element out of rendering elements displayed in the compositive rendering element displaying area 52 of the screen 50. The rendering control part 7 then displays in the details setting area 55 an opacity curve that is included in the chosen rendering element. The user may select a plurality of rendering elements in the compositive rendering element displaying area 52 so that the integrated opacity curve 78 is displayed.

Processing of excluding a value range is executed as rendering parameter integrating processing in the example described above. Other methods may be used to integrate rendering parameters, such as an alpha blending method in which coefficients associated with places in priority order are allocated, or a method in which the parameter larger in opacity value is used in the case of opacity and the parameter higher in priority order is used in the case of color.

While three types of priority processing, the extended area excluding processing, the area excluding processing, and the rendering parameter integrating processing, are used here, other priority processing methods than these may be defined.

Described next with reference to FIGS. 11A to 11D is a method of showing to the user how much a rendering element that is low in priority order contributes in a two-dimensional image that is obtained as a result of rendering processing when priority processing is executed.

The screen 50 of the display part 3 includes the image displaying area 51 for displaying a rendered medical image and the compositive rendering element displaying area 52 for displaying a compositive rendering element. In the compositive rendering element displaying area 52, the display control part 9 displays a list of the rendering elements 35 that are included in the set compositive rendering element 43. For instance, one row of a table displayed in the compositive rendering element displaying area 52 corresponds to one rendering element 35. A column 56 having a checkbox or toggle button for switching "on" and "off" of visibility is placed in the rows of the rendering elements 35. When the user uses this to set "on" to the visibility of a particular rendering element 35 alone and set "off" to the visibility of the other rendering elements 35, the rendering processing part 8 displays only the rendering result of an area to which the particular rendering element 35 contributes in the image displaying area 51.

A column 57 having a checkbox or toggle button for switching "on" and "off" of the enabled state is placed in the case where a difference between rendering results due to whether the priority processing is executed or not is to be visualized. When the user uses this to set "on" to the enabled state of a particular rendering element 35 alone and "off" to the enabled state of the rendering elements 35 above the particular rendering element 35, priority processing between the particular rendering element 35 and its upper rendering elements 35 (namely, modifications to mask areas or rendering parameters) is cancelled. A rendering result of the particular rendering element that has not been influenced by the priority processing is thus displayed by the rendering processing part 8.

For instance, when the user inputs an instruction to change the visibility or enabled state of one of the rendering elements 35, the rendering control part 7 may modify the compositive rendering element 43 following the input instruction (S 124) and execute priority processing based on the modified compositive rendering element 43 (S108), and the rendering processing part 8 may render an image on which the priority processing is reflected.

Figure 11A:
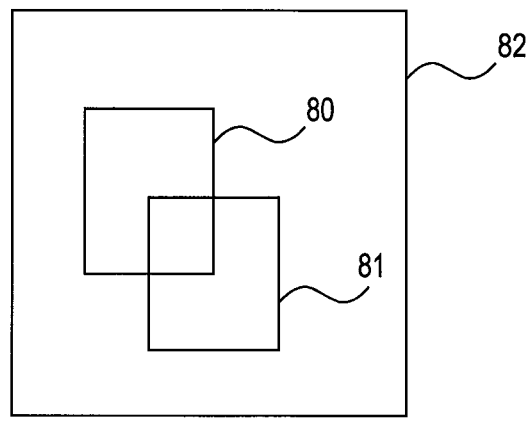
FIG. 11A is a diagram showing a state in which two overlapping mask areas are projected onto a two-dimensional image according to the embodiment of this invention.
Figure 11B:
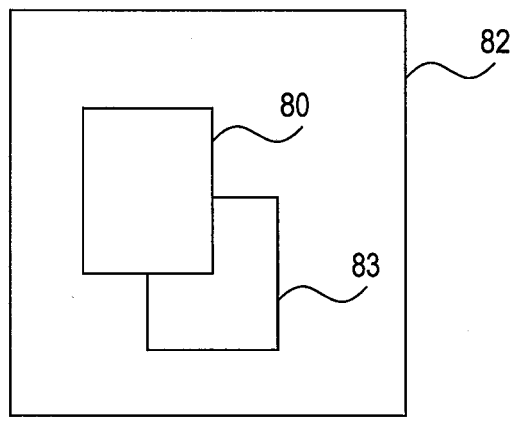
FIG. 11B is a diagram showing a state in which two mask areas processed by the extended area excluding processing are projected onto a two-dimensional image according to the embodiment of this invention.
Figure 11C:
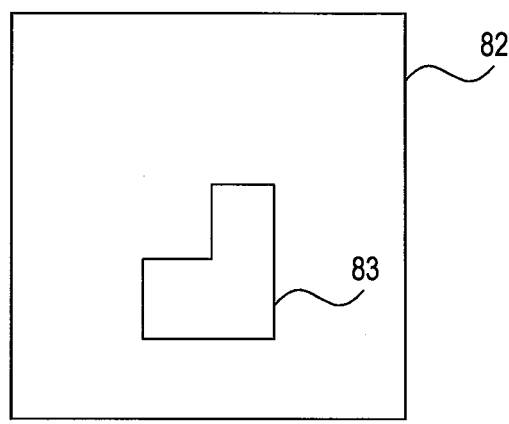
FIG. 11C is a diagram showing a state in which only mask areas of rendering elements low in priority order that have been processed by the extended area excluding processing are projected onto a two-dimensional image according to the embodiment of this invention.
Figure 11D:
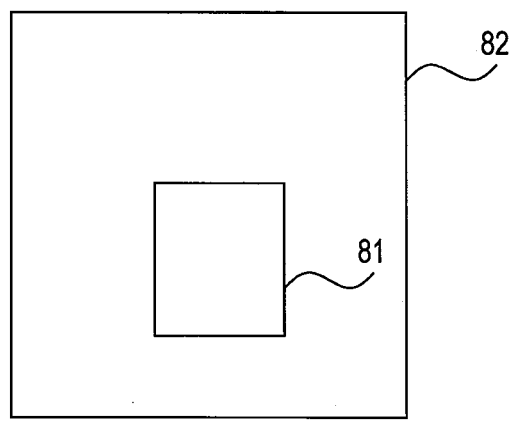
FIG. 11D is a diagram showing a state in which only mask areas of rendering elements low in priority order are projected onto a two-dimensional image, without executing the priority processing, according to the embodiment of this invention.

FIG. 11A illustrates areas 80 and 81 which are the projection onto a two-dimensional image 82 of masks set by two rendering elements, the rendering element A high in priority order and the rendering element B low in priority order. In the case where the extended area excluding processing is chosen as priority processing for the two rendering elements, an area is removed from the mask area 81 of the rendering element B which overlaps with an area that is an extension of the mask area 80 of the rendering element A in a direction parallel to the projection ray (i.e., a direction orthogonal to the screen of the two-dimensional image 82) as illustrated in FIG. 11B. This makes the rendering range of the rendering element B an area 83, which is the projection of a mask processed by the priority yielding processing onto the two-dimensional image. In the case where "off" is set to the visibility of the rendering element A and "on" is set to the visibility of the rendering element B at this point, only the area 83 is displayed as illustrated in FIG. 11C. In the case where "off" is set to the enabled state of the rendering element A at this point, the area 81 in which priority processing is not performed is displayed as illustrated in FIG. 11D.

The influence on a particular rendering element can similarly be shown to the user also when other types of priority processing are selected. The order of the rendering elements 35 on the list of the rendering elements 35 can be changed in the compositive rendering element displaying area 52. After the rendering elements 35 switch their places in order, the rendering control part 7 executes the priority processing again and the rendering processing part 8 updates the displayed image.

Described next with reference to FIG. 5 is a method of showing to the user a rendering element that is involved in rendering with respect to each pixel in a medical image generated by rendering processing. When the user clicks on a particular pixel in the image displaying area 51 of the screen 50 with the use of an input device such as a mouse, the rendering control part 7 displays a row 58 of a rendering element that is involved in the rendering of the pixel in an emphasized manner in the compositive rendering element displaying area 52. The emphasized display is accomplished by, for example, changing the color of the row 58, displaying a frame that surrounds the row 58, or displaying an icon that represents emphasis.

For instance, the rendering control part 7 may identify a mask area where a projection ray that reaches the pixel specified by the user passes through, and identify the rendering element 35 that is associated with the mask area (i.e., the rendering element 35 that includes the mask name 38 by which the mask area is specified) as a rendering element that is involved in the rendering of the pixel. The rendering control part 7 instructs the display part 3 to display the identified rendering element in an emphasized manner, and the display part 3 displays the identified rendering element in an emphasized manner following the instruction.

This method enables the user who is viewing a displayed two-dimensional image in order to modify a rendering element to easily find out which rendering element is to be modified.

The program that implements the functions, tables, files, and other types of information can be stored in a storage device such as a non-volatile semiconductor memory, a hard disk drive, or a solid state drive (SSD), or a computer-readable non-transitory data storage medium such as an IC card, an SD card, or a DVD.

This invention is not limited to the embodiment described above, and encompasses various modification examples. For instance, the embodiment has described this invention in detail for the ease of understanding, and this invention is not necessarily limited to a mode that includes all of the configuration described above. A part of the configuration of one embodiment may be replaced with the configuration of another embodiment, and the configuration of one embodiment may be used in combination with the configuration of another embodiment. In each embodiment, another configuration may be added to, deleted from or replace a part of the configuration of the embodiment.

What is claimed is:
1. An image display device, comprising:
a first processor;
first computer-readable storage media connected to the processor and which store:
a plurality of rendering elements each of which comprises a combination of rendering target information, which specifies a rendering target, and rendering settings information, which is referred to when the rendering target is rendered, and a respective place in a priority order assigned to each of the plurality of rendering elements,
where the rendering target information comprises data identification information for specifying three-dimensional signal value arrangements which are rendering targets, and mask information for specifying a rendering target area out of the three-dimensional signal value arrangements, and
where the rendering settings information comprises information for specifying a rendering method of rendering a two-dimensional image based on the three-dimensional signal value arrangements, and information for specifying a rendering parameter to be applied to the rendering method; and
a display part connected to the first processor,
wherein the first computer-readable storage media further store instructions that, when executed on the first processor, cause the first processor to:
determine, based on the rendering settings information and the mask information, whether or not priority processing in which one of the mask information or the rendering parameter is modified needs to be executed;

modify, when it is determined that the priority processing needs to be executed, the one of the mask information or the rendering parameter by executing the priority processing;

render a two-dimensional image based on the plurality of rendering elements that comprise the modified one of the mask information or the rendering parameter; and display the rendered two-dimensional image on the display part, wherein the priority processing comprises one of first priority processing, second priority processing, or third priority processing, where:

the first priority processing comprises removing, from the target area that is lower in the priority order out of two target areas that are at least partially on the same projection ray, a portion that is on the same projection ray, the second priority processing comprises removing, from the target area that is lower in the priority order out of two target areas that at least partially overlap with each other, the overlapping portion, and the third priority processing comprises creating a new rendering parameter by integrating two rendering parameters that are comprised in two rendering elements associated with two target areas that at least partially overlap with each other, and at least partially switching the two rendering parameters that are comprised in the two rendering elements to the new rendering parameter, and wherein the first computer-readable storage media further store instructions that, when executed on the first processor, cause the first processor to:

determine that the priority processing does not need to be executed for two rendering elements out of the plurality of rendering elements when two pieces of the rendering target information that are comprised in the two rendering elements specify the same three-dimensional signal value arrangement, two pieces of the rendering settings information that are comprised in the two rendering elements specify the same rendering method, and the two pieces of the rendering settings information specify the same rendering parameter;

determine, at least one of when the two pieces of the rendering target information do not specify the same three-dimensional signal value arrangement, when the two pieces of the rendering settings information do not specify the same rendering method, or when the two pieces of the rendering settings information do not specify the same rendering parameter, whether or not two target areas specified by the two pieces of the rendering target information are on the same projection ray;

determine, when the two target areas specified by the two pieces of the rendering target information are not on the same projection ray, that the priority processing does not need to be executed for the two rendering elements; and determine, when the two target areas specified by the two pieces of the rendering target information are on the same projection ray, that the priority processing needs to be executed for the two rendering elements; and when it is determined that the priority processing needs to be executed, the processor is further caused to:

execute the first priority processing for the two rendering elements when the two pieces of the rendering settings information comprised in the two rendering elements do not specify the same rendering method;

execute one of the first priority processing, the second priority processing, and the third priority processing for the two rendering elements when the two pieces of the rendering target information comprised in the two rendering elements specify the same three-dimensional signal value arrangement, and the target areas specified by the two pieces of the rendering target information overlap with each other; and execute one of the first priority processing and the second priority processing for the two rendering elements at least one of when the two pieces of the rendering target information comprised in the two rendering elements do not specify the same three-dimensional signal value arrangement, or when the target areas specified by the two pieces of the rendering target information comprised in the two rendering elements do not overlap with each other.

2. The image display device according to claim 1, wherein, when the respective rendering method specified by each of two pieces of rendering settings information comprised in the two rendering elements are both volume rendering, the rendering parameter specified by one of the two rendering elements that is higher in the priority order comprises first opacity information, which specifies at least one of opacity and color to be allocated to the signals values in a first range, the rendering parameter specified by one of the two rendering elements that is lower in the priority order comprises second opacity information, which specifies at least one of opacity and color to be allocated to the signals values in a second range, and the third priority processing includes:

creating third opacity information for allocating the first opacity information to a range where the first range and the second range overlap each other, for allocating the first opacity information to a range where the first range does not overlap with the second range, and for allocating the second opacity information to a range where the second range does not overlap with the first range, and then switching the first opacity information and the second opacity information to the third opacity information in a portion where the two mask areas overlap with each other.

3. The image display device according to claim 1, wherein the first computer-readable storage media further store instructions that, when executed on the first processor, cause the first processor to:

render, when an instruction to disable visibility is input for one of the plurality of rendering elements after the two-dimensional image is rendered based on the plurality of rendering elements that comprise the modified one of the mask information or the rendering parameter, a two-dimensional image based on the signal values within a target area that is specified by rendering elements other than the one of the plurality of rendering elements for which the instruction has been input, without rendering an image based on the signal values within a target area that is specified by the one of the plurality of rendering elements for which the instruction has been input; and cancel, when an instruction to disable an enabled state is input for one of the plurality of rendering elements after the two-dimensional image is rendered based on the plurality of rendering elements that comprise the modified one of the mask information or the rendering parameter, one of the modification of the mask information or the modification of the rendering parameter through the priority processing between the one of the plurality of rendering elements for which the instruction has been input and another rendering element, and render a two-dimensional image based on the one of the plurality of rendering elements for which the modification has been cancelled.

4. The image display device according to claim 1, wherein the first computer-readable storage media further store instructions that, when executed on the first processor, cause the first processor to:

when one of a plurality of pixels which are comprised in the rendered two-dimensional image is specified, display on the display part information identifying one of the plurality of rendering elements that is involved in rendering of the specified one of the pixels.

5. The image display device according to claim 4,
wherein the first computer-readable storage media further store instructions that, when executed on the first processor, cause the first processor to:
identify, as the one of the plurality of rendering elements that is involved in the rendering of the specified one of the pixels, one of the plurality of rendering elements that is associated with the target area where a projection ray reaching the specified one of the pixels passes through;
display a list of the plurality of rendering elements that have been referred to in order to render the two-dimensional image on the display part; and
display the rendering elements that are associated with the identified one of the plurality of rendering elements in an emphasized manner on the display part.

6. An image display system, comprising:
the image display device of claim 1;
an information management server which is coupled to the image display device via a network,
wherein the image display device further comprises a first communication interface which is coupled to the network and connected to the first processor,
wherein the information management server comprises a second communication interface which is coupled to the network, a second processor connected to the second communication interface, and second computer-readable storage media connected to the second processor which store at least one of:
a set that comprises a plurality of combinations of the data identification information and the mask information, a plurality of combinations of the information for specifying the rendering method and the information for specifying the rendering parameter, a plurality of combinations of the rendering target information and the rendering settings information, and a plurality of combinations of one rendering element and a respective place in the priority order, and a set that comprises a plurality of combinations of the rendering settings information and the respective place in the priority order, and
wherein the first computer-readable storage media and the second computer-readable storage media further store instructions that, when executed on the first processor and the second processor, cause the first processor and the second processor to;

store the plurality of rendering elements and the respective places in the priority order assigned to the plurality of respective rendering elements in the first computer-readable media of the image display device, based on information stored in the second computer-readable media of the information management server.

7. An image display method to be executed by an image display device, the image display device storing:
a plurality of rendering elements each of which comprises a combination of rendering target information, which specifies a rendering target, and rendering settings information, which is referred to when the rendering target is rendered, and holding a respective place in a priority order assigned to each of the plurality of rendering elements,
the rendering target information comprising data identification information for specifying three-dimensional arrangement of signal values which are rendering targets, and mask information for specifying a rendering target area out of the three-dimensional signal value arrangement, and
the rendering settings information comprising information for specifying a method of rendering a two-dimensional image based on the three-dimensional signal value arrangement, and information for specifying a rendering parameter to be applied to the rendering method,
the image display method comprising:
determining, based on the rendering settings information and the mask information, whether or not priority processing in which one of the mask information or the rendering parameter is modified needs to be executed;
modifying, when it is determined that the priority processing needs to be executed, the one of the mask information or the rendering parameter by executing the priority processing;
rendering a two-dimensional image based on the plurality of rendering elements that comprise the modified one of the mask information or the rendering parameter; and
displaying the rendered two-dimensional image,
wherein the priority processing comprises one of first priority processing, second priority processing, or third priority processing, where:
the first priority processing comprises removing, from the target area that is lower in the priority order out of two target areas that are at least partially on the same projection ray, a portion that is on the same projection ray,
the second priority processing comprises removing, from the target area that is lower in the priority order out of two target areas that at least partially overlap with each other, the overlapping portion, and
the third priority processing comprises creating a new rendering parameter by integrating two rendering parameters that are comprised in two rendering elements associated with two target areas that at least partially overlap with each other, and at least partially switching the two rendering parameters that are comprised in the two rendering elements to the new rendering parameter, and
wherein the determining of whether or not priority processing in which one of the mask information or the rendering parameter is modified needs to be executed includes;
determining that the priority processing does not need to be executed for two rendering elements out of the plurality of rendering elements when two pieces of the rendering target information that are comprised in the two rendering elements specify the same three-dimensional signal value arrangement, two pieces of the rendering settings information that are comprised in the two rendering elements specify the same rendering method, and the two pieces of the rendering settings information specify the same rendering parameter;

determining, at least one of when the two pieces of the rendering target information do not specify the same three-dimensional signal value arrangement, when the two pieces of the rendering settings information do not specify the same rendering method, or when the two pieces of the rendering settings information do not specify the same rendering parameter, whether or not two target areas specified by the two pieces of the rendering target information are on the same projection ray;

determining, when the two target areas specified by the two pieces of the rendering target information are not on the same projection ray, that the priority processing does not need to be executed for the two rendering elements; and determining, when the two target areas specified by the two pieces of the rendering target information are on the same projection ray, that the priority processing needs to be executed for the two rendering elements, and wherein the modifying the one of the mask information or the rendering parameter by executing the priority processing includes;

executing the first priority processing for the two rendering elements when the two pieces of the rendering settings information comprised in the two rendering elements do not specify the same rendering method;

executing one of the first priority processing, the second priority processing, and the third priority processing for the two rendering elements when the two pieces of the rendering target information comprised in the two rendering elements specify the same three-dimensional signal value arrangement, and the target areas specified by the two pieces of the rendering target information overlap with each other; and executing one of the first priority processing and the second priority processing for the two rendering elements at least one of when the two pieces of the rendering target information comprised in the two rendering elements do not specify the same three-dimensional signal value arrangement, or when the target areas specified by the two pieces of the rendering target information comprised in the two rendering elements do not overlap with each other.

8. The image display method according to claim 7, wherein, when the respective rendering method specified by each of the two pieces of rendering settings information comprised in the two rendering elements are both volume rendering, the rendering parameter specified by one of the two rendering elements that is higher in the priority order comprises first opacity information, which specifies at least one of opacity and color to be allocated to the signals values in a first range, the rendering parameter specified by one of the two rendering elements that is lower in the priority order comprises second opacity information, which specifies at least one of opacity and color to be allocated to the signals values in a second range, and the third priority processing includes:

creating third opacity information for allocating the first opacity information to a range where the first range and the second range overlap each other, for allocating the first opacity information to a range where the first range does not overlap with the second range, and for allocating the second opacity information to a range where the second range does not overlap with the first range, and then switching the first opacity information and the second opacity information to the third opacity information in a portion where the two mask areas overlap with each other.

9. The image display method according to claim 7, further comprising:

rendering, when an instruction to disable visibility is input for one of the plurality of rendering elements after the two-dimensional image is rendered based on the plurality of rendering elements that comprise the modified one of the mask information or the rendering parameter, a two-dimensional image based on the signal values within a target area that is specified by rendering elements other than the one of the plurality of rendering elements for which the instruction has been input, without rendering an image based on the signal values within a target area that is specified by the one of the plurality of rendering elements for which the instruction has been input; and canceling, when an instruction to disable an enabled state is input for one of the plurality of rendering elements after the two-dimensional image is rendered based on the plurality of rendering elements that comprise the modified one of the mask information or the rendering parameter, one of the modification of the mask information or the modification of the rendering parameter through the priority processing between the one of the plurality of rendering elements for which the instruction has been input and another rendering element, and rendering a two-dimensional image based on the one of the plurality of rendering elements for which the modification has been cancelled.

10. The image display method according to claim 7, further comprising:

displaying, when one of a plurality of pixels which are comprised in the rendered two-dimensional image is specified, information identifying one of the plurality of rendering elements that is involved in rendering of the specified one of the pixels.

11. The image display method according to claim 10, wherein the displaying of the information identifying one of the plurality of rendering elements that is involved in rendering of the specified one of the pixels comprises:

identifying, as the one of the plurality of rendering elements that is involved in the rendering of the specified one of the pixels, one of the plurality of rendering elements that is associated with the target area where a projection ray reaching the specified one of the pixels passes through;

displaying a list of the plurality of rendering elements that have been referred to in order to render the two-dimensional image; and displaying the rendering elements that are associated with the identified one of the plurality of rendering elements in an emphasized manner.

12. The image display method according to claim 7, wherein the image display device is coupled to a network, wherein an information management server is coupled to the image display device via the network, wherein the information management server stores at least one of a set that comprises a plurality of combinations of the data identification information and the mask information, a plurality of combinations of the information for specifying the rendering method and the information for specifying the rendering parameter, a plurality of combinations of the rendering target information and the rendering settings information, and a plurality of combinations of one rendering element and the place in the priority order, and a set that comprises a plurality of combinations of the rendering settings information and the place in the priority order, and wherein the image display method further comprises:
storing, in the image display device, the plurality of rendering elements and the places in the priority order assigned to the plurality of respective rendering elements, based on information stored in the information management server.

* * * * *